United States Patent

Beckers

[11] Patent Number: 5,993,485
[45] Date of Patent: Nov. 30, 1999

[54] BLADDER PORTAL

[76] Inventor: Michael B. Beckers, 402 Banner Rd., Pullman, Wash. 99163

[21] Appl. No.: 09/022,439

[22] Filed: Feb. 12, 1998

[51] Int. Cl.$^6$ ..................................................... A61F 2/04
[52] U.S. Cl. ............................... 623/12; 600/30; 128/769
[58] Field of Search ................................ 623/11, 12, 14; 600/29–32; 604/8–9, 41, 280, 337; 128/760, 763, 769

[56] References Cited

U.S. PATENT DOCUMENTS

| | | | |
|---|---|---|---|
| 2,510,766 | 6/1950 | Surface | 600/32 |
| 3,447,533 | 9/1969 | Spicer | 600/32 |
| 4,217,664 | 8/1980 | Faso | 623/12 |
| 4,228,550 | 10/1980 | Sackind | 623/12 |
| 4,338,937 | 7/1982 | Lerman | 600/32 |
| 4,781,176 | 11/1988 | Ravo | 623/12 |
| 5,234,408 | 8/1993 | Griffith | 623/12 |
| 5,370,690 | 12/1994 | Barrett | 623/12 |
| 5,403,264 | 4/1995 | Wohlers et al. | 600/32 |
| 5,512,032 | 4/1996 | Kulisz et al. | 623/12 |
| 5,749,826 | 5/1998 | Faulkner | 600/29 |

FOREIGN PATENT DOCUMENTS 3613699  10/1987  Germany ........................ 600/29

*Primary Examiner*—Bruce E. Snow
*Attorney, Agent, or Firm*—Staas & Halsey LLP

[57] ABSTRACT

A bladder portal including a fistula threaded on the inside to accept a seatable screw. The fistula includes a flange fitting inside the bladder and a flange positioned outside the body. The screw is removed to allow urine to flow.

1 Claim, 2 Drawing Sheets

BLADDER PORTAL

BACKGROUND OF THE INVENTION

1. Field of the Invention

The present invention is directed to a device that substitutes for the urethra and sphincter muscles that control the release of urine from a bladder.

2. Description of the Related Art

For many different reasons, one of which is cancer, the urethra and sphincter muscles that allow urine to flow from an animal bladder can become dysfunctional or lost. What is needed is a device that can substitute for these organs.

SUMMARY OF THE INVENTION

It is an object of the present invention to provide a fluid portal as a substitute for the urethra and sphincter muscles.

It is another object of the present invention to provide an artificial bladder that includes a portal.

The above objects can be attained by a controllable liquid portal that can substitute for the urethra and sphincter muscles in an animal such as a dog or human.

These together with other objects and advantages, which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

The present invention is designed for a bladder application where the urethra and sphincter muscles have been lost. The invention provides a controllable portal for urine. It is human operated by unscrewing the bolt to drain the bladder.

Figure 3:
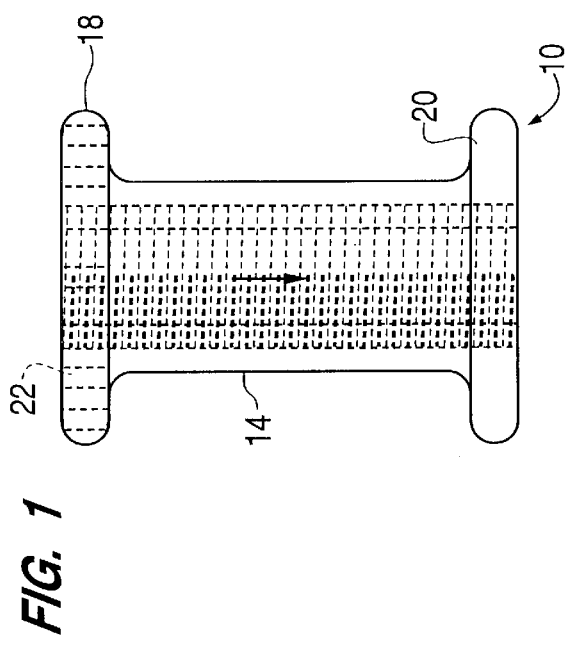
FIG. 3 depicts a side view of a screw that controls flow through the fistula.
Figure 2:
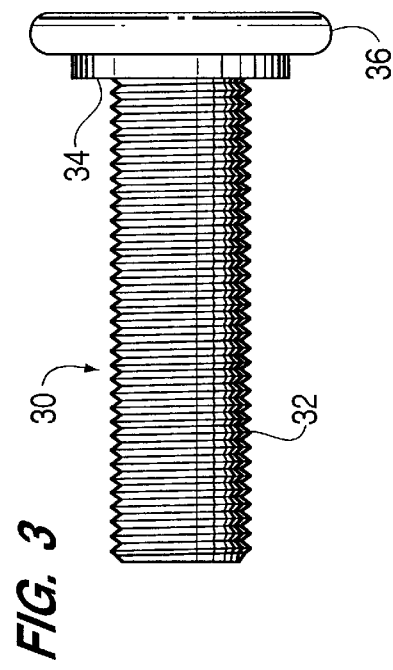
FIG. 2 depicts an end view of the fistula.
Figure 1:
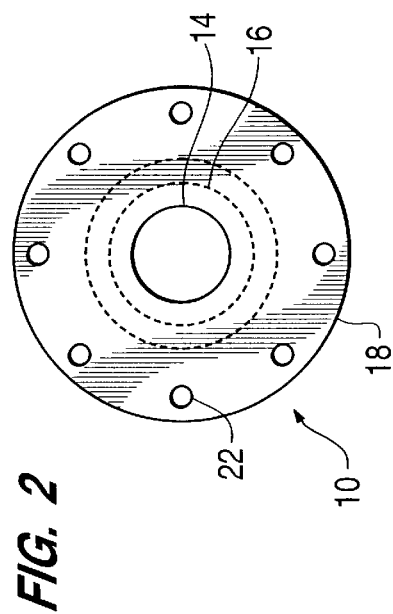
FIG. 1 depicts a side view of a fistula according to the present invention.

The portal of the present invention, depicted in FIGS. 1–3, is made from a non-bioreactive substance such as Polyesterene, commonly called TEFLON, although the invention can be made from other substances such as stainless steel. The portal includes a fistula 10 as depicted in FIGS. 1 and 2 and a flow control device 30 depicted in FIG. 3.

The fistula 10 is essentially a spool shaped apparatus that includes a hollow shaft 14 with interior threads 16 and two end flanges 18 and 20 (see FIG. 1). The exterior surface of the fistula preferably has a satin finish where the machine marks are lightly sanded, not polished. One of the flanges 18 includes a plurality of suture holes 22, preferably eight, that pass through the flange 18 and which are used to secure the fistula to the exterior of the abdominal wall. The other flange 20 fits inside the bladder and it has no suture holes as this would tend to tear the bladder tissue. Each flange includes a ring and a corner radius that curves in to meet the shaft 14. The surface of this area is also a satin finish which allows a good grip and seal but does not irritate the tissue. Tension from the surrounding tissue pushes against the smaller radius of the fistula leaving the rings at either end to overlap or overhang the tissue which keeps it from moving in or out. The suture holes 22, at one end 18, aid retention while the surrounding tissue heals. As the tissue heals it tightens around the fistula 10 creating retention tension. As the tissue heals it also grows into the satin surface of the fistula 10, which is slightly rough, filling the peaks and valleys in the surface providing a tight seal. Some leakage may occur after the installation.

The flow control device 30 is essentially a screw or bolt/plug which includes a threaded shaft 32, a seal seat 34 and a head 36 that sized to be gripped by the hand. The seat 34 of the screw plug 30 is screwed into the fistula 10 until the seat 32 seals against the flange 18 to keep fluid from flowing out of the bladder and is removed to allow urine to flow out of the bladder. Other types of flow control devices could be used such as a petcock.

The fistula 10 is made from a cylindrical TEFLON stock which is first mounted in a spindle lathe. A portion of the stock, of approximately at least 30 cm, is turned down to a diameter of 14-mm the outside diameter of the flanges 18 and 20. Then an area of approximately 15-mm in length is turned down to a diameter of approximately 8-mm to form the exterior of the shaft 14. The interior corner of each flange, which is created by the 8-mm diameter section meeting the larger diameter, is filleted at a radius of 0.9-mm. The stock is the cut at both ends normal to the center axis of the stock. This cut is made twice, by a blade, at approximately 2-mm from the edge of the smaller radius cut on both sides. Two rings or flanges 18 and 20 now exist at either end of the spool with a 14-mm diameter and a thickness of 2-mm. The outer edges of the rings are then cambered to a radius of approximately 1-mm. The fistula hole 16, approximately 4-mm in diameter, is then drilled in the center of the spool, down the length of the spool and exiting the other end. Then holes 22 are then drilled on one end (18). The holes 22 are approximately 0.8-mm in diameter and are placed at a radial distance of approximately 6-mm.

The bolt 30 is cut from the same stock on a lathe. An approximately 30-mm portion is turned down to approximately 12-mm forming the diameter of the head 36. Starting at one end of this cut, the bolt is turned to a diameter of approximately 6-mm for a distance of approximately 20.5-mm forming shaft 32. The bolt 30 is next turned down to 9-mm in radius for 1-mm in length forming the seat 34. The next cut is made by a blade cross-sectionally at a distance of 2-mm from the last radius cut removing the stock from shaft 32. Another cross-sectional cut is made at the other end where the smallest radius cut began releasing the head 36 from the stock. The head 36 is then cambered to a radius of 1-mm and knurled to make it easier to grab.

Next a matching tap and die set is then chosen, both the fistula 10 and bolt 30 are threaded and then screwed together to check the fit.

Figure 4:
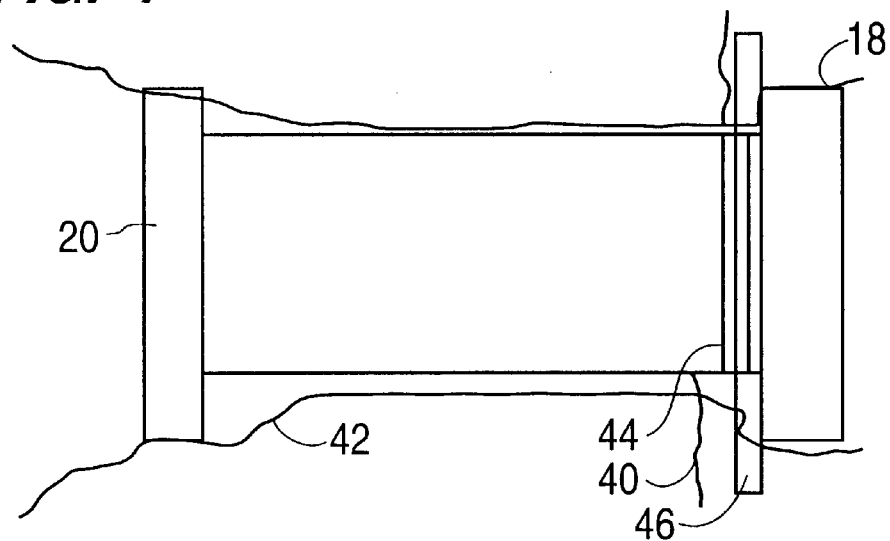
FIGS. 4 and 5 depict the fistula of the invention situated in a body.
Figure 5:
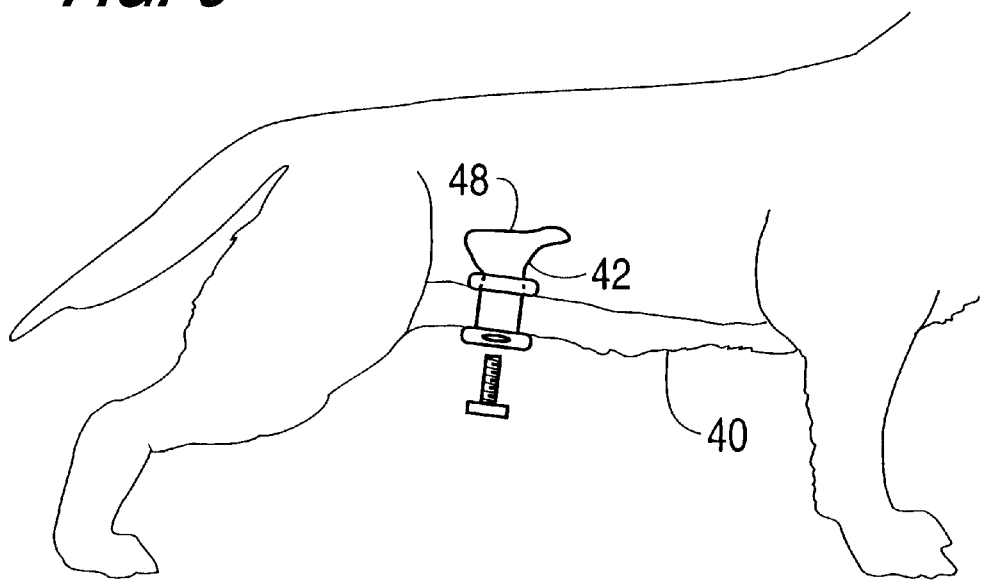

The fistula 10 is inserted in an abdominal wall hole and into a bladder hole created by surgery. After being inserted, the two flanges 18 and 20 are positioned in the respective tissue to set on either side of the abdominal wall tissue 40 and the bladder tissue 42 as depicted in FIGS. 4 and 5. The fistula can also include a groove 44 and O-ring 46 as depicted in FIG. 4 that help to seal the fistula to the abdominal wall tissue. The flange 18 the eight holes drilled radially is placed outside the body. These holes 22 are then used to place sutures through the wall tissue to further aid in the retention of the portal. Tension from surrounding tissues increases over time providing further stability allowing the animal a reasonable amount of normal activity.

Typically the portal is used with an existing bladder. However, it is also possible to use the portal with a bladder made from another tissue such as intestinal tissue. It is also possible to use a completely artificial, synthetic bladder material, such as TEFLON, as a bladder bag held in the body cavity. The kidney ducts (not shown) are sutured into the bag 48 and the bag 48 is secured in the body cavity. The fistula 10 would be sealed to the bag using the O-ring 46 and groove 44 with the bag material between the flange 18 and the O-ring 46.

The many features and advantages of the invention are apparent from the detailed specification and, thus, it is intended by the appended claims to cover all such features and advantages of the invention which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A bladder portal, comprising:

a spool shaped fistula having a first end positionable inside the bladder and a second end adapted to be positioned outside a body, said fistula made as a unit from a single homogenous material throughout said fistula and comprising:

a hollow shaft threaded on an interior for substantially an entire interior length of said shaft;

a first flange extending from the shaft on an outside surface via a first radial corner having a radius and adapted to be positioned inside the bladder; and a second flange extending from the shaft on the outside surface via a second radial corner having the radius and adapted to be positioned outside the body, said second flange including radially positioned circular suture holes; and a headed screw of the material and openably closing the said hollow shaft on the second end outside the body, said screw comprising:

a threaded shaft having a screw length substantially equal to the interior length of said hollow shaft;

a liquid seal seat extending from the shaft, seating against said second flange producing a liquid seal; and an exposed, knurled head extending from the seat and adapted to be gripped by a hand.

* * * * *